US009765796B2

(12) United States Patent
Norris

(10) Patent No.: US 9,765,796 B2
(45) Date of Patent: Sep. 19, 2017

(54) DEVICES AND METHODS FOR REDUCING NOISE IN A BLOWER HOUSING

(71) Applicant: KONINKLIJKE PHILIPS N.V., Eindhoven (NL)

(72) Inventor: Russell Hughes Norris, Murrysville, PA (US)

(73) Assignee: Koninklijke Philips N. V., Eindhoven (NL)

( * ) Notice: Subject to any disclaimer, the term of this patent is extended or adjusted under 35 U.S.C. 154(b) by 648 days.

(21) Appl. No.: 14/357,369

(22) PCT Filed: Nov. 13, 2012

(86) PCT No.: PCT/IB2012/056384
§ 371 (c)(1),
(2) Date: May 9, 2014

(87) PCT Pub. No.: WO2013/072846
PCT Pub. Date: May 23, 2013

(65) Prior Publication Data
US 2014/0314544 A1    Oct. 23, 2014

Related U.S. Application Data

(60) Provisional application No. 61/559,741, filed on Nov. 15, 2011.

(51) Int. Cl.
*F04D 29/66* (2006.01)
*F04D 29/42* (2006.01)
*F04D 29/44* (2006.01)

(52) U.S. Cl.
CPC ......... *F04D 29/665* (2013.01); *F04D 29/422* (2013.01); *F04D 29/4226* (2013.01); *F04D 29/441* (2013.01); *F04D 29/667* (2013.01)

(58) Field of Classification Search
USPC .................................................. 415/204, 206
See application file for complete search history.

(56) References Cited

U.S. PATENT DOCUMENTS

| | | | | |
|---|---|---|---|---|
| 2,956,736 A * | 10/1960 | Mayer, Jr. | ............. | F04D 29/422 181/277 |
| 3,545,890 A * | 12/1970 | Larson | .................. | F04D 23/008 415/168.1 |
| 3,687,360 A * | 8/1972 | Prew | ....................... | B04B 11/02 138/39 |
| 5,527,150 A * | 6/1996 | Windhofer | ............ | F04D 29/161 415/55.1 |
| 6,176,689 B1 | 1/2001 | Bumbel et al. | | |
| 6,471,475 B1 * | 10/2002 | Sasu | ..................... | F04D 29/444 415/211.2 |
| 6,622,724 B1 | 9/2003 | Truitt et al. | | |
| 8,951,005 B2 * | 2/2015 | Smeulers | ............... | F04D 29/422 415/119 |
| 2005/0074326 A1 | 4/2005 | Curtis | | |

FOREIGN PATENT DOCUMENTS

WO    WO2011062633    5/2011

* cited by examiner

*Primary Examiner* — Mark Laurenzi
*Assistant Examiner* — Shafiq Mian

(57) ABSTRACT

Devices and methods for reducing noise of a blower reduce and/or substantially block the exchange of gas within the blower housing from an area of a generally high-velocity flow of gas to an area of a comparatively lower-velocity flow of gas, for example near the outlet of the blower housing.

18 Claims, 18 Drawing Sheets

DEVICES AND METHODS FOR REDUCING NOISE IN A BLOWER HOUSING

CROSS-REFERENCE TO PRIOR APPLICATIONS

This application is the U.S. National Phase application under 35 U.S.C. §371 of International Application Ser. No. PCT/IB2012/056384, filed on Nov. 13, 2012, which claims the benefit of U.S. Application Ser. No. 61/559,741, filed on Nov. 15, 2011. These applications are hereby incorporated by reference herein.

BACKGROUND

1. Field

The present disclosure pertains to devices and methods for reducing noise in a blower housing and, in particular, for blowing gas from an inlet to an outlet in such a way that vortices of gas at or near the outlet are reduced and/or transitions in gas velocity within the blower housing and/or at or near the outlet are less abrupt.

2. Description of the Related Art

It is well known that centrifugal blowers have many useful applications, including, but not limited to, medical and therapeutic applications. It is well known that some types of respiratory therapy involve the delivery of a pressurized flow of breathable gas to the airway of a subject. It is known that centrifugal blowers in operation may produce one or both of tonal noise and/or broadband noise in a range of (high) human auditory sensitivity. It is known that centrifugal blowers having time-varying impeller speed, outlet flow, and/or other operating parameters may produce similarly time-varying noise.

SUMMARY

Accordingly, it is an object of one or more embodiments of the present invention to provide a device for blowing gas from an inlet to an outlet. The device comprises an impeller, a blower housing configured to house the impeller; an impeller mount disposed within the blower housing, the impeller mount being configured to rotatably mount the impeller within the blower housing, wherein the blower housing is configured to form a first chamber and a second chamber, wherein the impeller is disposed within the first chamber such that the first chamber is divided from the second chamber at or near the second side of the impeller, and such that as the impeller rotates within the first chamber, gas imparted with energy from the impeller is expelled from the impeller. The impeller has a first side and a second side, the first side being configured to impart energy to gas responsive to the impeller being rotated, the second side being opposite the first side and having a generally circular shape. The impeller has a circumference. The second chamber is in fluid communication with the first chamber through an opening between the first chamber and the second chamber. The opening is formed radially outward from an axis of rotation of the impeller to an outer edge of the impeller such that gas that has been expelled radially from the impeller in the first chamber flows around the outer edge of the impeller and into the second chamber through the opening. The second chamber includes an outlet such that pressurized gas that flows into the second chamber is discharged from the blower housing through the outlet, the outlet being formed in the second chamber in an outlet area of the second chamber corresponding to an arc portion of the circumference of the impeller. The blower housing is further configured such that the opening between the first chamber and the second chamber is substantially blocked at or near the outlet area such that substantially no gas is exchanged between the first chamber and the second chamber through the opening at or near the outlet area.

It is yet another aspect of one or more embodiments of the present invention to provide a method for reducing noise of a device for blowing gas from an inlet to an outlet. The method comprises receiving gas through an inlet of a blower housing that is formed to include a first chamber and a second chamber; rotating an impeller on an impeller mount disposed within the blower housing; imparting energy to the received gas in the first chamber, responsive to the impeller rotating; fluidly communicating gas expelled radially from the impeller, responsive to the impeller rotating, such that expelled gas flows around the outer edge of the impeller, from the first chamber to the second chamber via an opening; discharging the expelled gas from the second chamber, responsive to the impeller rotating, through an outlet of the second chamber that is formed in an outlet area, wherein the outlet corresponds to an arc portion of a circumference of the impeller; and substantially blocking part of the opening between the first chamber and the second chamber such that substantially no gas is exchanged through the opening at or near the outlet area.

It is yet another aspect of one or more embodiments to provide a system configured to reduce noise of a device for blowing gas from an inlet to an outlet. The system comprises means for receiving gas into a blower housing that is formed to include a first chamber and a second chamber; mounting means for rotating an impeller, wherein the mounting means is disposed within the blower housing; rotating means for imparting energy to the received gas in the first chamber; communicating means for fluidly communicating gas expelled radially from the rotating means, such that expelled gas flows around the outer edge of the rotating means, from the first chamber to the second chamber; discharging means for discharging the expelled gas from the second chamber, that is formed in a discharge area of the second chamber, wherein the discharging means corresponds to an arc portion of a circumference of the rotating means; and blocking means for substantially blocking part of the communicating means between the first chamber and the second chamber such that substantially no gas is exchanged through the communicating means at or near the discharge area.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
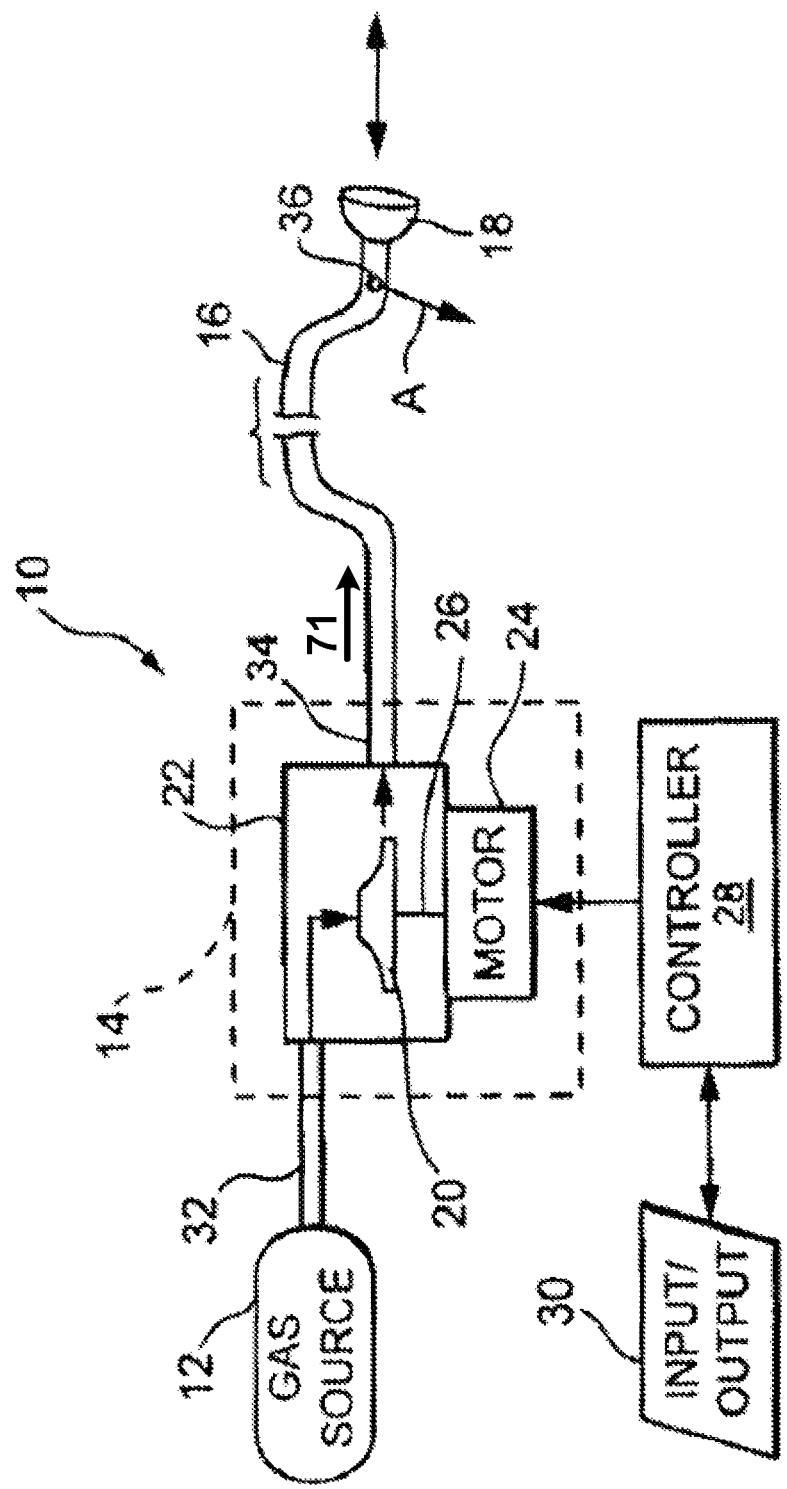
FIG. 1 is a schematic view of a pressure support system, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Applications of the noise-reduction techniques described herein may include various fields of technology, including but not limited to medical applications, home appliances, kitchen appliances, consumer electronics, centrifugal pumps and/or fans, heating and/or cooling applications, water jets, mixers, blenders, turbines, and/or other fields of technology and/or other applications. An exemplary embodiment of a medical application in which these noise-reduction techniques may be applied is a respiratory therapy device, such as, e.g., a ventilator and/or continuous positive airway pressure (CPAP) device, used e.g. to supply a substantially constant positive pressure to the airway of a subject, through a pressurized flow of breathable gas. Though this exemplary embodiment is not intended to be limiting in any way, this disclosure will repeatedly use a respiratory therapy device in order to clarify various aspects of the claimed invention.

FIG. 1 schematically illustrates a pressure support system 10, in accordance with one or more embodiments. Pressure support system 10 includes a source of breathing gas 12, such as air from the ambient atmosphere or a tank, oxygen from a tank or oxygen concentrator, a mixture of gases, with or without nebulized medication or the like, as known in the art. Pressure support system 10 also includes a pressure generator 14 that receives gas from the gas source and elevates the pressure of the gas to produce a flow of breathable gas at a pressure that is greater than the ambient, i.e. atmospheric, pressure. A patient circuit 16, which is typically a flexible conduit, carries the pressurized flow of breathable gas to the patient. A patient interface device 18 coupled to the patient circuit communicates the flow of breathable gas from patient circuit 14 to the airway of the patient. Patient interface device 18 is any device suited for this purpose, such as a nasal mask, nasal/oral mask, total face mask, nasal cannula, trachea tube, endotracheal tube, hood, or other conventional patient respiratory gas delivery system as known in the art.

Pressure generator 14 includes an impeller 20 disposed within a housing 22. The details of impeller 20 are discussed below with reference to, at least, FIGS. 2-4, and the details of housing 22 are discussed below with reference to, at least, FIGS. 5-6. A motor 24 coupled to a drive shaft 26 rotates impeller 20. The operation of motor 24 is controller by a controller 28. Controller 28 is any device, system, or assembly suitable to operate motor 24. In its simplest form, controller 28 can be a power supply operated by an on/off switch. Of course, this allows for little control over the speed of motor 24 to set the desired pressure to be output by pressure generator 14. To this end, conventional controls, which are schematically illustrated as input/output device 30, are provided for providing inputs to controller 28, for example to select the desired output pressure, and, hence, the operating speed of motor 24. Of course, using input/output device 30 and controller 28 to control the operation of pressure support system 10 is also contemplated. Such operation can include setting and displaying information, such as current pressure settings, alarms, and usage of the system. Exemplary controls include an on/off control for pressure support system 10, a timing type control for selective operation of pressure support system 10, selectors for the desired pressures to be delivered by pressure support system 10 and other controls and displays as known in the art.

Pressure generator 14 receives breathable gas from gas source 12 at (gas) inlet 32 and elevates the pressure of the received gas. The flow of breathable gas having an elevated pressure is output at a (gas) outlet 34. In the illustrated embodiment, an output flow 71 of breathable gas is delivered via patient circuit 16 to the patient via patient interface 18. In this embodiment, which illustrates a single-limb patient circuit, patient circuit 16 includes an exhaust vent 36 proximate to patient interface device 18. Exhaust vent 36 allows exhaled gas from the patient to vent to atmosphere as indicated by arrow A.

Figure 2:
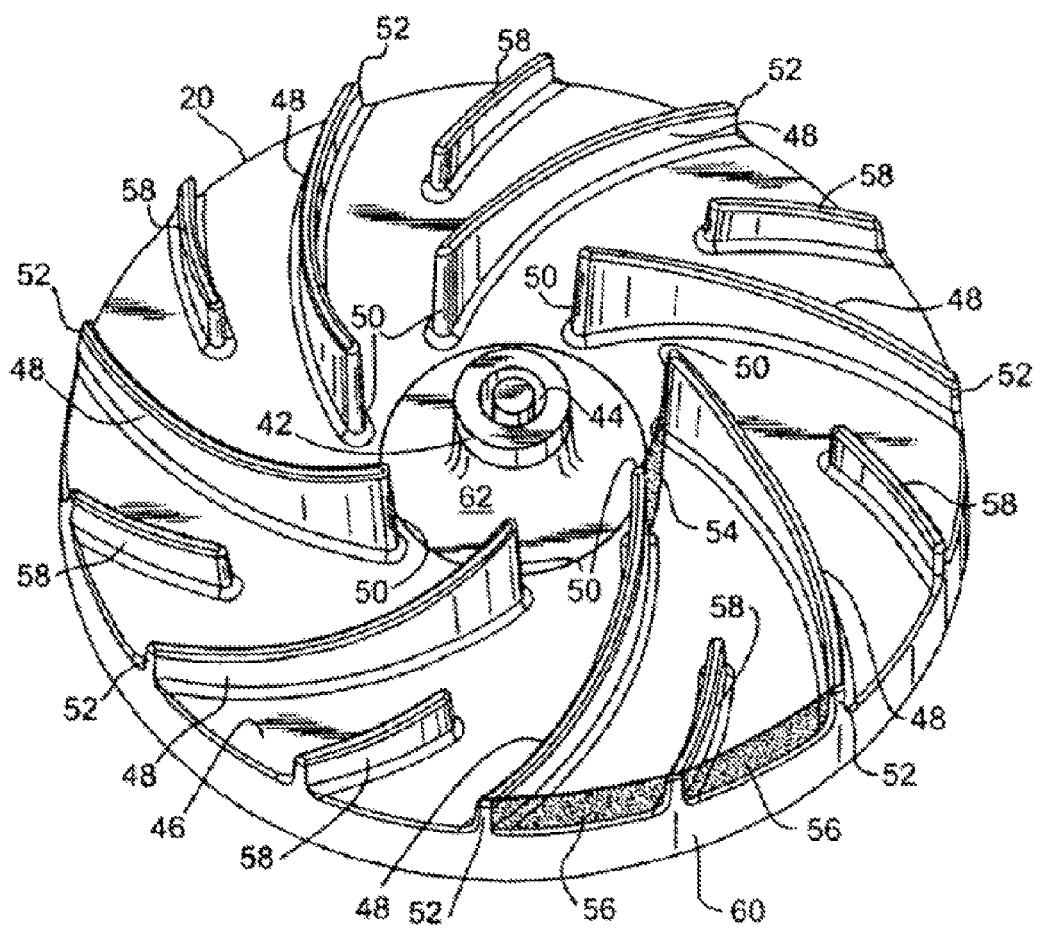
FIG. 2 is a perspective view of an impeller for use in the pressure support system of FIG. 1.
Figure 3:
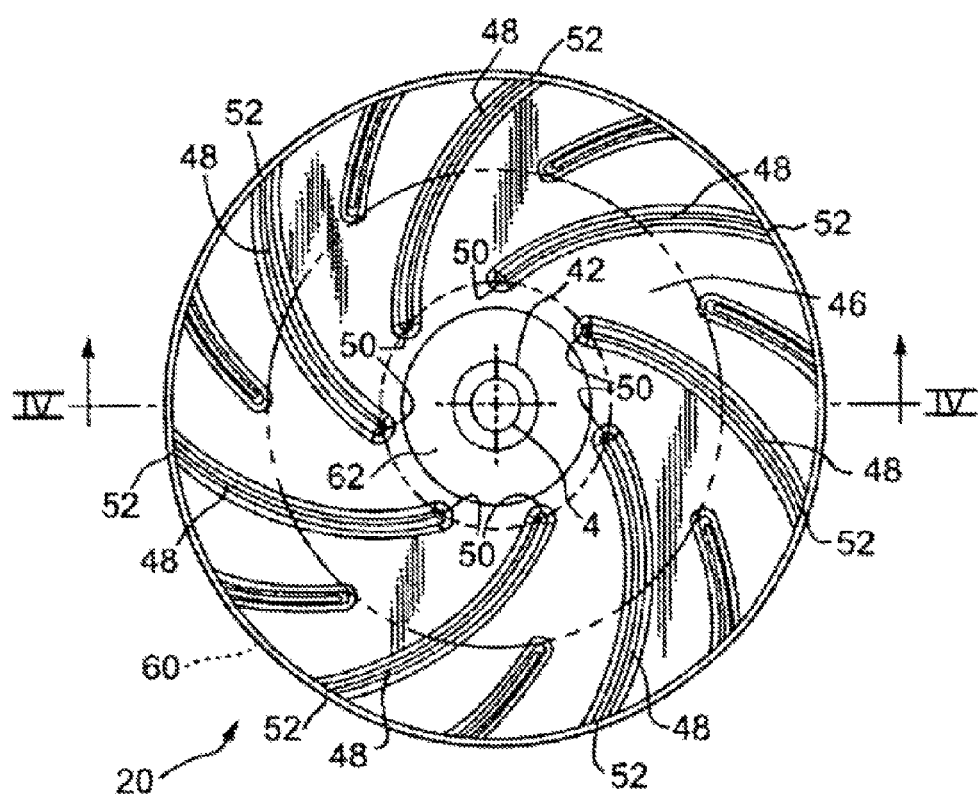
FIG. 3 is a top plan view of the impeller of FIG. 2.
Figure 4:
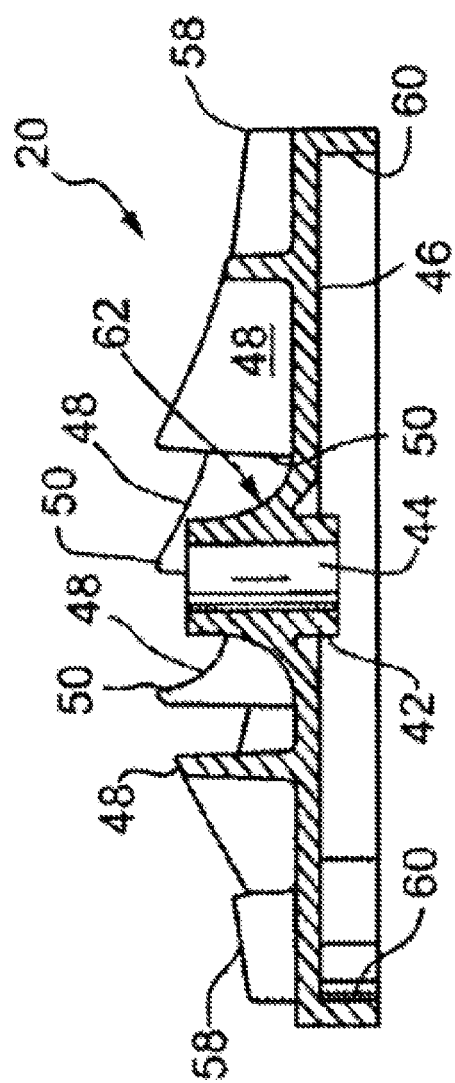
FIG. 4 is a cross-sectional view of the impeller of FIGS. 2 and 3 taken along line IV-IV of FIG. 3.

As shown in FIGS. 2-4, impeller 20 includes a hub 42 with a bore 44 therethrough so that the hub and impeller can receive drive shaft 26 and be attached thereto in a conventional fashion Impeller 20 includes an impeller body 46 attached to hub 42 and extending generally radially from hub 42 to a perimeter of impeller 20. Impeller 20 includes a plurality of impeller blades 48 attached to an upper face of impeller body 46. Individual ones of blades 48 may be curved backward. Individual ones of blades 48 may extend from a leading end 50, positioned generally adjacent hub 42, to a trailing end 52 at a perimeter of the impeller 20.

Blades 48 are designed for delivering a substantially constant pressure gas to outlet 34 even if the rate of flow of gas in the patient circuit varies. This aspect may be achieved, at least in part, by the shape and geometry of the blades. Specifically, blades 48 define a plurality of inlet areas generally adjacent hub 42 and a plurality of outlet areas located generally adjacent the perimeter of impeller 20. One such inlet area 54 and outlet area 56 are illustrated in FIG. 2 with the illustrated outlet area 56 corresponding to the illustrated inlet area 54. The corresponding inlet and outlet areas are those inlet and outlet areas defined between the same adjacent blades 48. Individual ones of the inlet areas are defined as the area at the radius of leading end 50 of adjacent blades 48 bounded by a height of the leading end of the adjacent blades and the surface of impeller body 46. Individual ones of the outlet areas are defined as the area at the radius of the trailing end 52 of the adjacent blades 48 bounded by the height of the trailing end of the adjacent blades and the surface of the impeller body.

In the impeller body 46 of one or more exemplary embodiments, individual ones of the inlet areas are substantially equal to individual corresponding ones of the outlet areas. Maintaining substantially equality of inlet areas to corresponding outlet areas is believed to provide a substantially constant pressure gas at outlet 34, despite fluctuations in the flow rate typically encountered in a pressure support system. In one or more embodiments, outlet areas are maintained substantially equal to the corresponding inlet areas by having blades 48 decrease in height as the blades extend radially outward from hub 42. It is to be understood, however, that there are other techniques for maintaining equal corresponding inlet and outlet areas. In the illustrated embodiment, a radial area between adjacent blades, which is an area between adjacent blades at a radial position from hub 42 and that is bounded by the height of the adjacent blades at the radial position and the one face of the impeller body, is substantially the same over a length of the pair of adjacent blades. Thus, for individual pairs of blades, the radial position along the length of both blades has substantially the same area.

Pressure generator 14 may include one or more means for minimizing the noise of impeller 20. The one or more noise minimizing means may include a plurality of partial blades 58 attached to the upper face of impeller body 46, with individual ones of partial blades 58 being disposed between a pair of adjacent blades 48. A partial blade 58 extends from a position radially outward from inlet areas 54 about the midpoint of impeller body 46 to the perimeter of impeller 20. Partial blades 58 act on the flow of gas to minimize the noise created by impeller 20 during operation.

Impeller 20 is preferably a one-piece, injection-molded, thermoplastic member. Of course, impeller 20 can be made from multiple components, using various techniques and materials. For smooth operation of impeller 20, the impeller may need to be balanced after manufacture. Conventional balancing of impellers and wheels, in general, requires that material be added to or deleted from the impeller or wheel, typically at the perimeter of the structure. As shown, impeller 20 includes a balancing means to simplify the balancing operation. The balancing means includes an annular skirt 60, attached to impeller body 46 at the perimeter of impeller 20, with skirt 60 extending axially from the opposite face of impeller body 46 as blades 48 and partial blades 58. Skirt 60 provides a convenient location for selectively removing material for balancing impeller 20 without affecting the fluid flow in the impeller.

FIG. 4 additionally illustrates that hub 42 includes a smooth outer surface 62 curving radially outward toward inlet area 54. Smooth outer surface 62 is designed to guide the fluid flow from the inlet, which is centered above hub 42, to inlet areas 54 on impeller 20 and further help minimize the noise associated with the operation of impeller 20.

Figure 5:
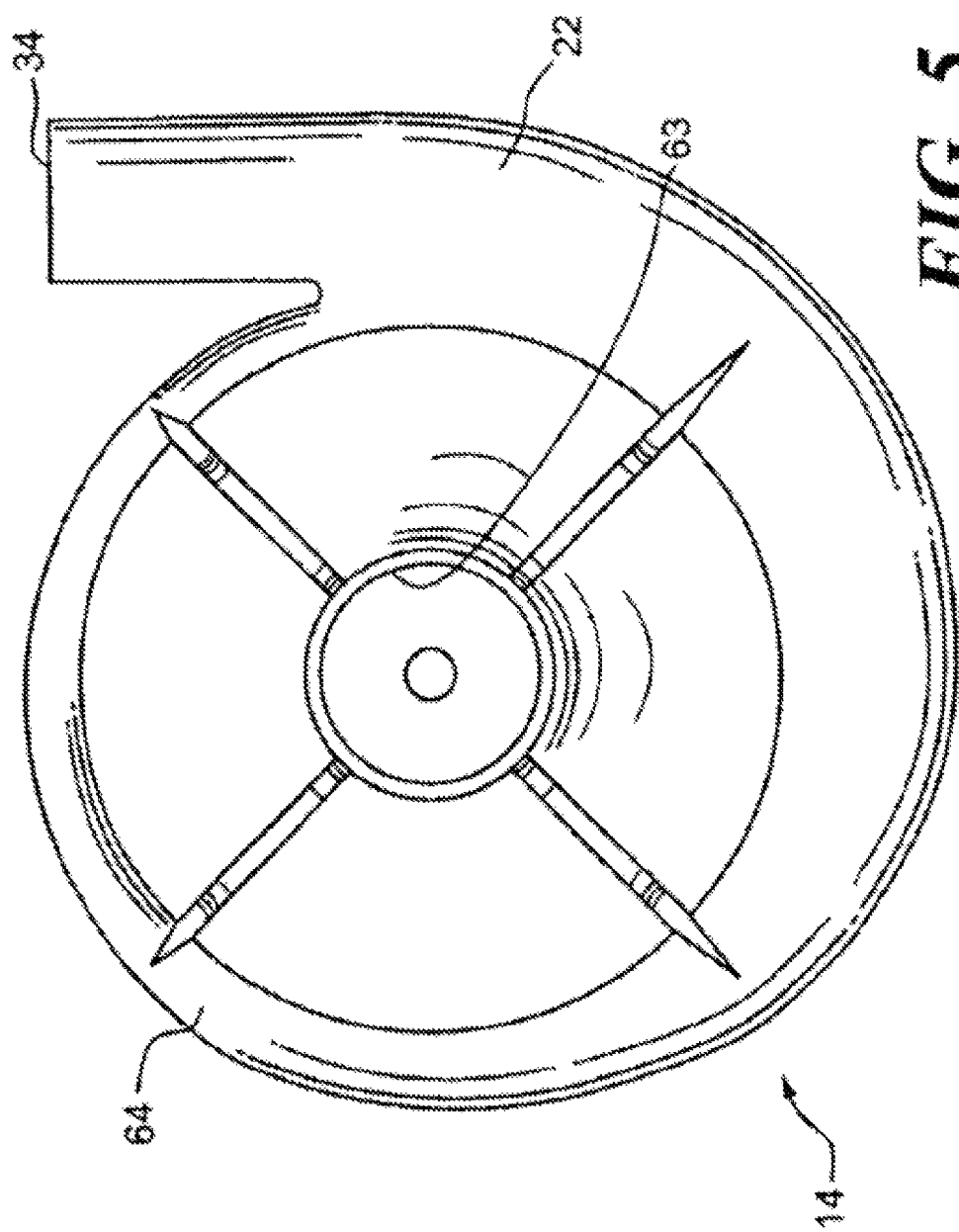
FIG. 5 is a top plan view of a pressure generator of the pressure support system of FIG. 1 including the impeller of FIGS. 2-4.
Figure 6:
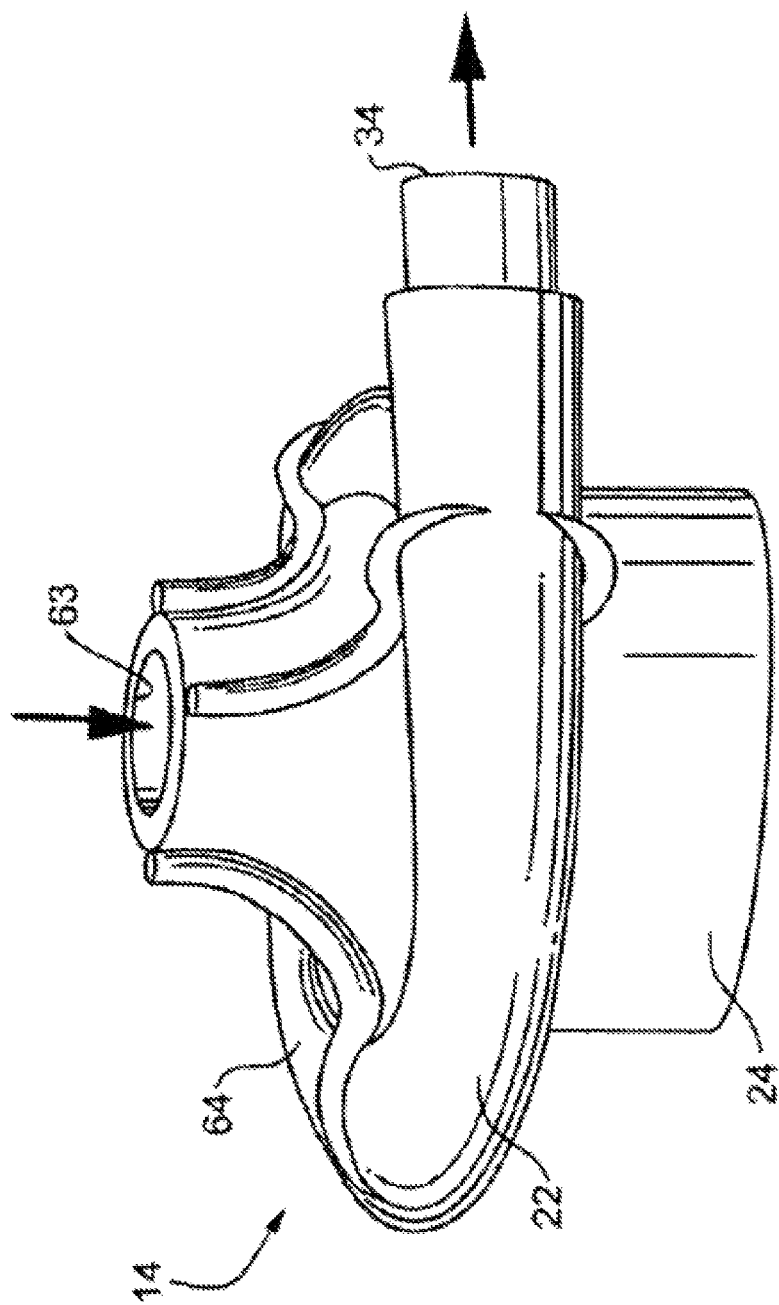
FIG. 6 is a perspective view of the pressure generator of FIG. 5.

Pressure generator 14 is shown in greater detail in FIGS. 5-6. As shown in FIGS. 5 and 6, housing 22 includes a gas flow inlet 63 located above the hub of the impeller so that gas enters housing 22 and is directed to the inlet areas of the impeller blades. As illustrated in FIG. 6, housing 22 in pressure generator 14 follows the contour of the height of the blades 48 extending radially of impeller 20. The gap between the upper portion of the individual blades 48 and housing 24 is minimized. This gap may be maintained constant along the length of blades 48. Conforming housing 24 to the shape of blades 48 is believed to further assist in maintaining a substantially constant pressure through conventional flow rates for respiratory therapy.

Additionally, as shown in FIGS. 5-6, housing 22 includes a gas outlet channel 64 that extends circumferentially around impeller 20. In some embodiments, gas outlet channel 64 is provided with an arithmetically increasing cross-sectional area. The increasing cross-sectional area of the gas outlet channel 64 results in an increased radius from leading end 50 of individual blades 48 to gas outlet channel 64 about the circumference of impeller 20. In some embodiments, gas outlet channel 64 has a substantially constant cross-sectional area.

Additional information on noise reduction techniques in respiratory therapy devices may be found in U.S. Pat. No. 6,622,724, entitled "Impeller And A Pressure Support System And Method Using Such An Impeller," and issued Sep. 23, 2003, which is hereby incorporated by reference into the present application in its entirety.

Figure 7:
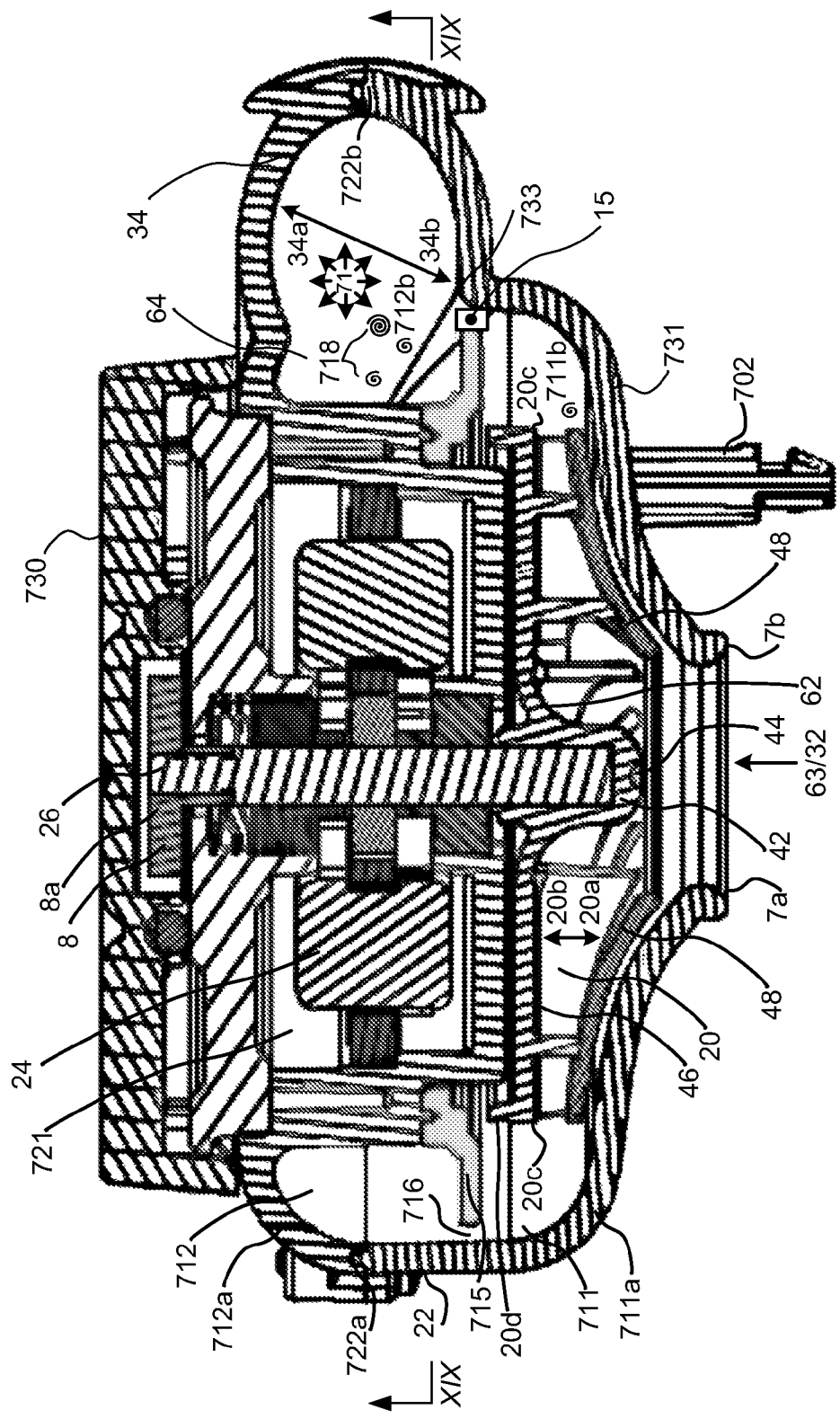
FIG. 7 schematically illustrates a device for blowing gas from an inlet to an outlet, according to certain embodiments.

FIG. 7 schematically illustrates a cross-sectional view of a device 70 for blowing gas from inlet 32 to outlet 34, according to certain embodiments. In some embodiments of the present technology, a device similar to or the same as device 70 may be used to propel a fluid, a gas, and/or a combination thereof. Device 70 may, e.g., be implemented as, integrated with, combined with, connected with, and/or operating in conjunction with a respiratory therapy device. For example, device 70 may be used as a ventilator, pressure support device (PAP/CPAP/BiPAP®/etc.), and/or other medical application that may benefit from blowing gas from an inlet to an outlet.

Device 70 in FIG. 7 includes one or more of impeller 20, inlet 32, outlet 34, housing 22, impeller mount 8, motor 24, and/or other components. Inlet 32 is located at an inlet side 731 of housing 22. Outlet 34 is located on an outlet side 730 of housing 22 Impeller 20 includes a first side 20a, configured to impart energy to gas responsive to impeller 20 being rotated, and a second side 20b being opposite first side 20a. As impeller 20 is rotated, blades 48 impart energy to the surrounding gas. When impeller 20 is installed within housing 22, first side 20a is closer to inlet side 731 of housing 22 than to outlet side 730. Second side 20b of impeller 20 is closer to outlet side 730 of housing 22 than to inlet side 731. Second side 20b has a generally circular shape, having a circumference 20c. Impeller 20 includes hub 42 with bore 44 therethrough so that hub 42 and impeller 20 can receive drive shaft 26 and be attached thereto in a conventional fashion. As depicted in FIG. 7, the plane of rotation of impeller 20 may be substantially perpendicular to the page as viewed, i.e. coming out of the page and going through the page.

During operation device 70 receives gas through inlet 32 at inlet side 731 of housing 22. Drive shaft 26 is disposed within housing 22 and configured to rotatably drive impeller 20 within housing 22 Impeller mount 8 may include drive shaft 26, rotating portion 8a, and/or other components. For example, drive shaft 26 may include additional components to couple drive shaft 26 to impeller 20, in a conventional fashion. Additional components may be used to couple drive shaft 26 with motor 24, such that motor 24 operates to rotate drive shaft 26. Housing 22 includes a motor compartment 721, such that motor 24 is disposed within motor compartment 721. The position of impeller mount 8 within housing 22 may be fixated, for example on outlet side 730 of housing 22. Impeller 20 is attached centrally to drive shaft 26, such that rotation of drive shaft 26 causes similar rotation of impeller 20. Device 70 includes an external mount 702, which may be used to fixate device 70 in a larger system, such as, e.g., pressure support system 10.

Housing 22 is configured to form a first chamber 711 and a second chamber 712. First chamber 711 and second chamber 712 are formed by a first housing portion 711a, a second housing portion 712a, and/or other components. In some embodiments, first housing portion 711a is connected to second housing portion 712a by mating elements 722a and 722b. This connection may be made permanent, or substantially permanent via adhesive, ultrasonic weld, bonding, snap fit, press fit, friction fit, fasteners, and/or other mechanisms for mating components. First housing portion 711a is located on inlet side 731 of housing 22. Second housing portion 712a is located on outlet side 730 of housing 22. At a ledge 733 gas outlet channel 64 is separated from the connection between first housing portion 711a and second housing portion 712a. Inlet 32 is formed in an inlet area, indicated between 7a and 7b in FIG. 7, of first chamber 711 of housing 22. Inlet area continuously spans from 7a to 7b in FIG. 7. Housing 22 is configured to house impeller 20 within first chamber 711. First chamber 711 may be divided from second chamber 712 at or near second side 20b of impeller 20. Second chamber 712 includes outlet 34 in an outlet area, indicated between an outlet area edge 34a and an outlet area edge 34b in FIGS. 7-8, such that gas that flows into second chamber 712 is discharged from housing 22 through outlet 34 as gas flow 71.

As impeller 20 rotates, gas received through inlet 32 is energized by blades 48 of impeller 20, and is expelled outwardly from impeller 20 toward the periphery of first chamber 711. Housing 22 acts as a guide to this gas, and guides it into second chamber 712 through an opening 716. This opening 716 provides for fluid communication between first chamber 711 and second chamber 712. Opening 716 is formed radially outward from an axis of rotation of impeller 20 to an outer edge of impeller 20 such that expelled gas flows around the outer edge of impeller 20 and into second chamber 712 through opening 716. Opening 716 may be annular or generally annular in shape. Opening 716 may be formed by different parts of housing 22, such as, e.g., first housing portion 711a, second housing portion 712a, impeller 20, and/or by parts or components carried by housing 22 or constituent components thereof, such as, e.g., a baffle plate 715. Note that opening 716 may be formed beyond the entirety or beyond a fraction of the outer edge of impeller 20, and need not be confined to the location depicted the label '716' in FIG. 7.

In some embodiments, housing 22 includes baffle plate 715, arranged such that opening 716 extends beyond baffle plate 715, as depicted in FIG. 7. In some embodiments that lack a baffle plate, impeller 20 may extend outward further than depicted in FIG. 7, such that an impeller lip 20d is arranged similarly close to the inner edge of housing 22 as baffle plate 715 does in FIG. 7, such that the gap between impeller lip 20d and the inner edge of housing 22 effectively acts as opening 716. As depicted in FIG. 7, first chamber 711 is separated from second chamber 712 by second side 20b of impeller 20, and by baffle plate 715.

Figure 15:
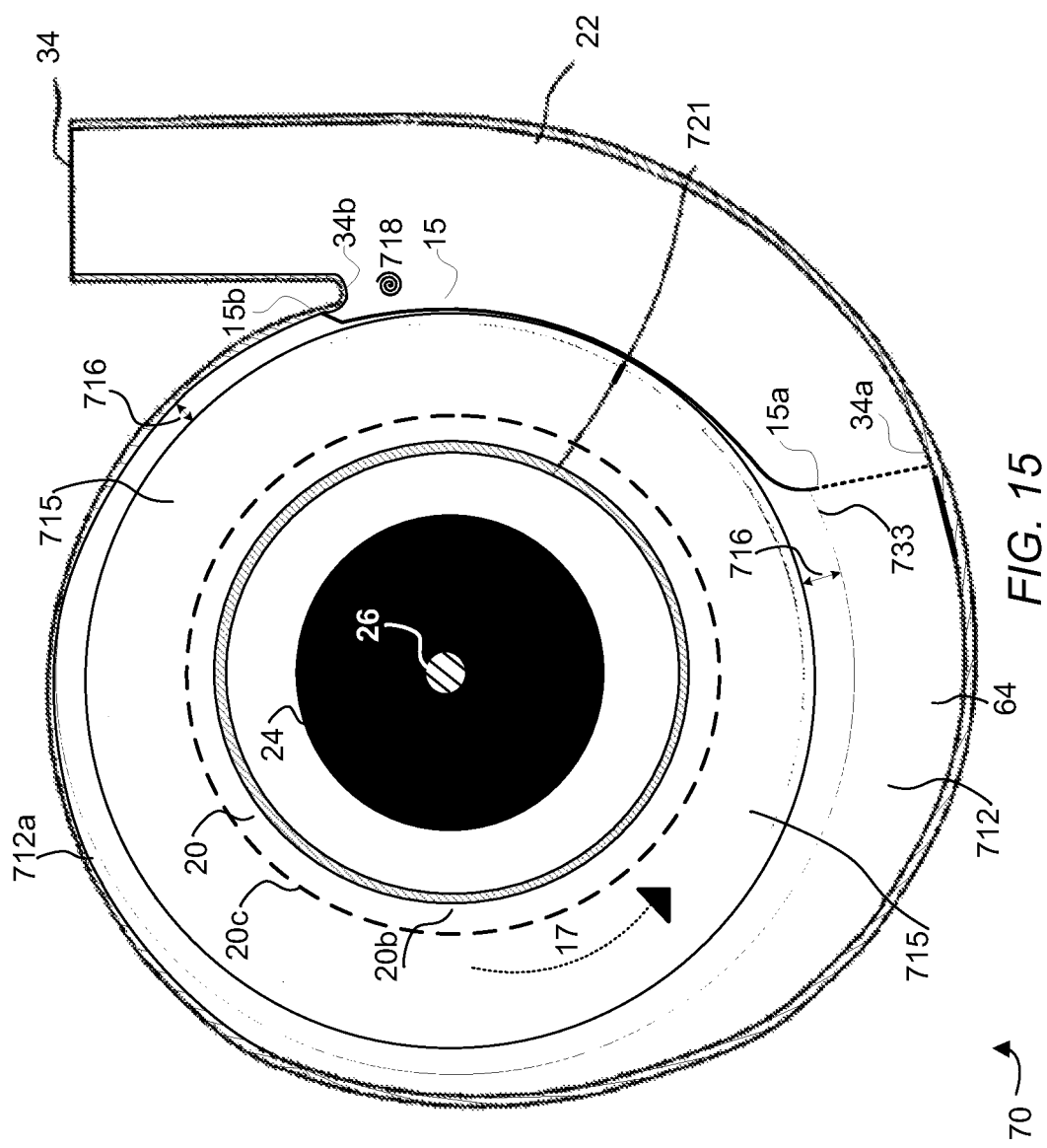
FIG. 15 is a cross-sectional view of the device of FIG. 7, taken along line XIX-XIX of FIG. 7.

FIG. 15 is a cross-sectional view of device 70, taken along line XIX-XIX of FIG. 7. Impeller 20 is viewed from second side 20b. Drive shaft 26 is shown centrally, as is motor 24 within motor compartment 721. As depicted in FIG. 15, baffle plate 715 extends beyond impeller circumference 20c, leaving opening 716 between baffle plate 715 and the inner edge of housing 22. Gas outlet channel 64 may be separated from opening 716 at ledge 733. Note that, in some embodiments, gas outlet channel 64 may have a substantially constant cross-sectional area, and/or another arithmetically progressing shape of its cross-sectional area. Housing 22 in FIG. 15 is configured such that opening 716 between first chamber 711 (not shown) and second chamber 712 is substantially blocked at or near outlet 34 (and/or a portion of the outlet area of second chamber 712 indicated between edge 34a and edge 34b) such that substantially no gas is exchanged between first chamber 711 and second chamber 712 through opening 716 at or near outlet 34 (and/or a portion of the outlet area of second chamber 712, indicated between edge 34a and edge 34b). Substantially blocking opening 716 at or near outlet 34, e.g. via an obstruction 15, may reduce vortices 718 in the outlet area. In some embodiments, opening 716 may be substantially blocked at or near outlet 34 (and/or the outlet area) by an extended baffle plate that extends beyond the depiction of baffle plate 715 in FIG. 15. Alternatively, and/or simultaneously, opening 716 may be substantially blocked by another member, component, and/or element extending either outward beyond impeller circumference 20c, inwards from the inner edge of housing 22, and/or both.

Referring to FIG. 15, substantially blocking opening 716 at or near outlet 34 may reduce one or both of tonal noise and/or broadband noise in a range of high human auditory sensitivity. Such a range may be about 20 Hz to about 15 kHz, and/or any portion thereof. For example, the range may be about 200 Hz to 400 Hz, about 240 Hz to 600 Hz, about 220 Hz to 800 Hz, and/or other ranges of human auditory sensitivity. In one or more embodiments, the noise generated by operating device 70 or a device similar to device 70 may include a time-varying component that corresponds to similarly time-varying operating conditions of the device. For example, device 70 may alter the speed of impeller 20 intermittently, and/or according to any pattern or periodicity, e.g. in substantial synchrony to the breathing pattern of a subject. In such an embodiment, substantially blocking opening 716 at or near outlet 34 may reduce the time-varying component of the noise generated by operating device 70.

Figure 8:
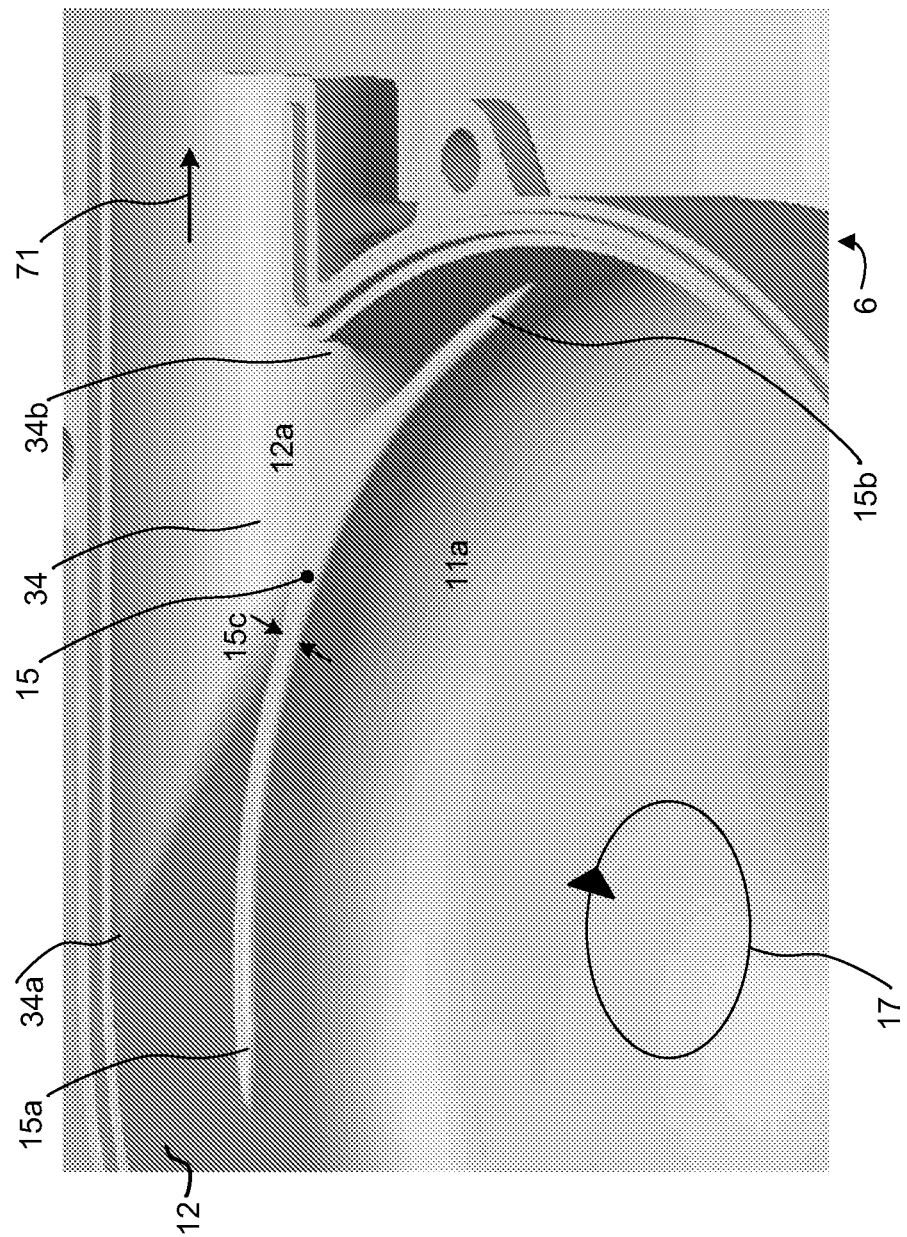
FIG. 8 schematically illustrates a part of a blower housing, according to certain embodiments.

By way of illustration, FIG. 8 depicts an obstruction 15 that is included in or near housing 22, second chamber 712, and/or outlet 34. Outlet 34 is located in an outlet area corresponding to an arc portion of circumference 20c of impeller 20, indicated between edge 34a and edge 34b. Obstruction 15 substantially blocks and/or reduces gas exchange between a high-velocity flow of gas 711b, which rotates as indicated by direction 17, and a lower-velocity flow of gas 712b. Vortices 718 are caused by a collision of high-velocity flow of gas 711b with lower-velocity flow of gas 712b (i.e. a lower velocity compared to the velocity of flow of gas 711b), particularly at or near edge 34b, which is located downstream from edge 34a relative to a direction 17 of the rotation of impeller 20. In some embodiments, obstruction 15 spans an arc length ranging between about 30 and 120 degrees, between about 45 and 90 degrees, about 45 degrees, about 60 degrees, about 90 degrees, and/or other arc length of circumference 20c of impeller 20 at or near the outlet area. In some embodiments, obstruction 15 spans at least about half, about a third, about two-thirds, about three-quarters, at least the entirety, and/or another ratio or fraction of the arc portion corresponding to outlet 34. As depicted in FIG. 8, obstruction 15 spans from a tip 15a to a tip 15b, covering at least the entirety of the arc portion corresponding to outlet 34, from edge 34a to edge 34b.

In some embodiments, obstruction 15 is disposed and/or (integrally) formed inside housing 22 and connecting the interior of housing 22 at or near tip 34b, substantially coplanar with impeller 20, intruding a particular arc length of the circumference of impeller 20 into housing 22, corresponding to at least a portion of outlet 34. The particular arc length may be about 45 degrees, about 60 degrees, about 90 degrees, about 120 degrees, and/or another arc length. For some applications, including, e.g., medical applications, having a gap around obstruction 15 in opening 716 at or near outlet 34 of about less than 0.050 inch, about less than 0.020 inch, about less than 0.010 inch, and/or less than another gap threshold size is adequate to substantially block the exchange of gas as described above. In some embodiments, there may be no such gap as an obstruction is connected and/or formed integrally with housing 22, baffle plate 715, and/or other components of device 70, such that a solid connection acts to obstruct the exchange of gas at or near outlet 34 or the outlet area. In some embodiments, for some applications, a thickness 15c of obstruction 15 may be about less than 0.060 inch, about less than 0.040 inch, about less than 0.020 inch, and/or another thickness. In some embodiments, obstruction 15 may, along its entire length or along a section between tip 15a and tip 15b, span substantially the entire depth of second chamber 712 as defined in a plane substantially perpendicular to the rotation of impeller 20. Alternatively, or simultaneously, obstruction 15 may span less than the entire depth of second chamber 712.

Figure 9:
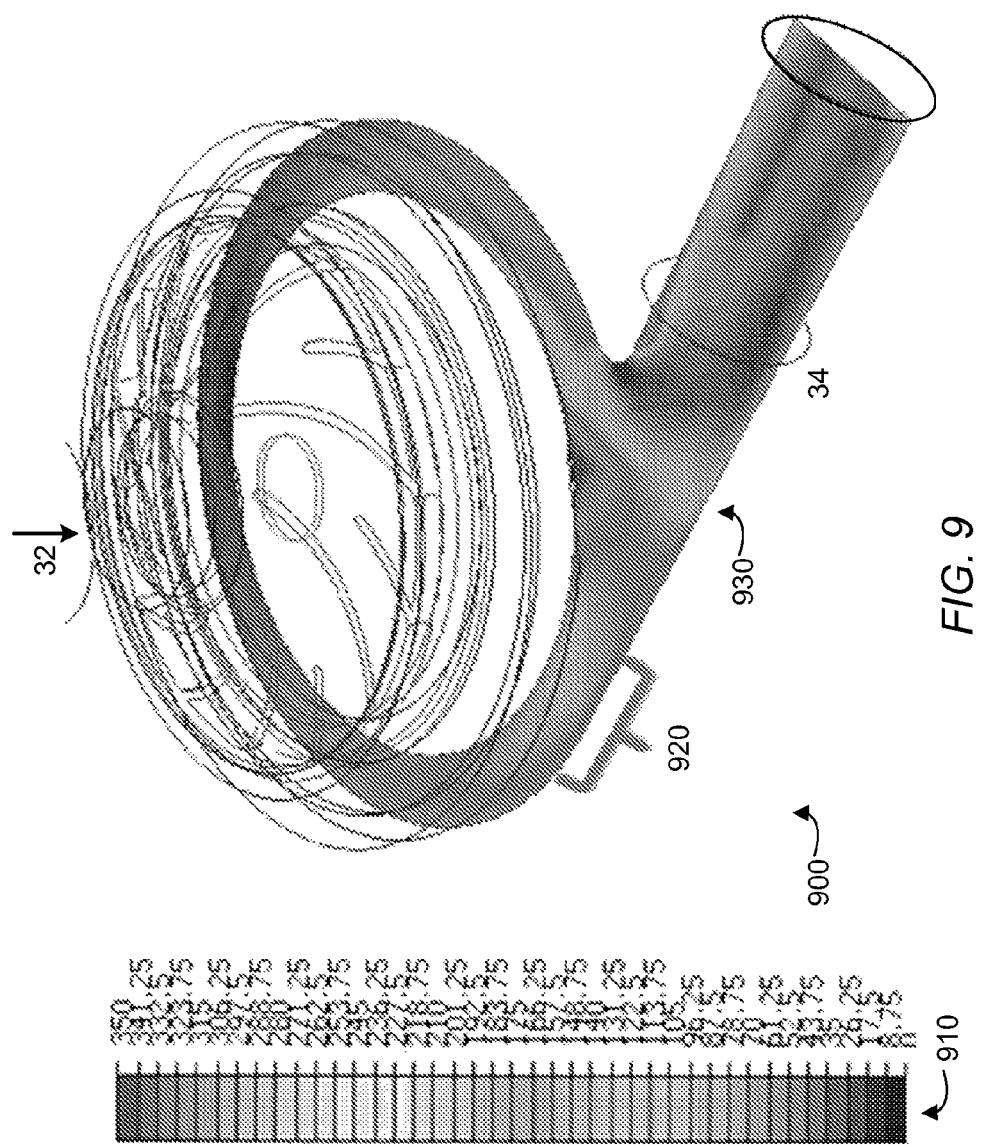
FIG. 9 illustrates a computational fluid dynamics (CFD) analysis of the velocity of a flow of gas in a blower housing during operation.

FIG. 9 illustrates a computational fluid dynamics (CFD) analysis of the velocity of flowing gas in a blower housing during operation, resulting in spatial distribution 900. This analysis does not include an obstruction similar to or substantially the same as obstruction 15 of FIG. 8. Referring to FIG. 9, vertical scale 910 indicates gas velocity, in inches per second, ranging from 0 to 350 inch/s. In the analysis for FIG. 9, area 930 indicates a relatively abrupt transition from comparatively lower velocity gas flow to comparatively higher velocity gas flow, near outlet 34. Area 920 indicates a particular proportion of comparatively lower velocity gas flow near/upstream from outlet 34.

Figure 10:
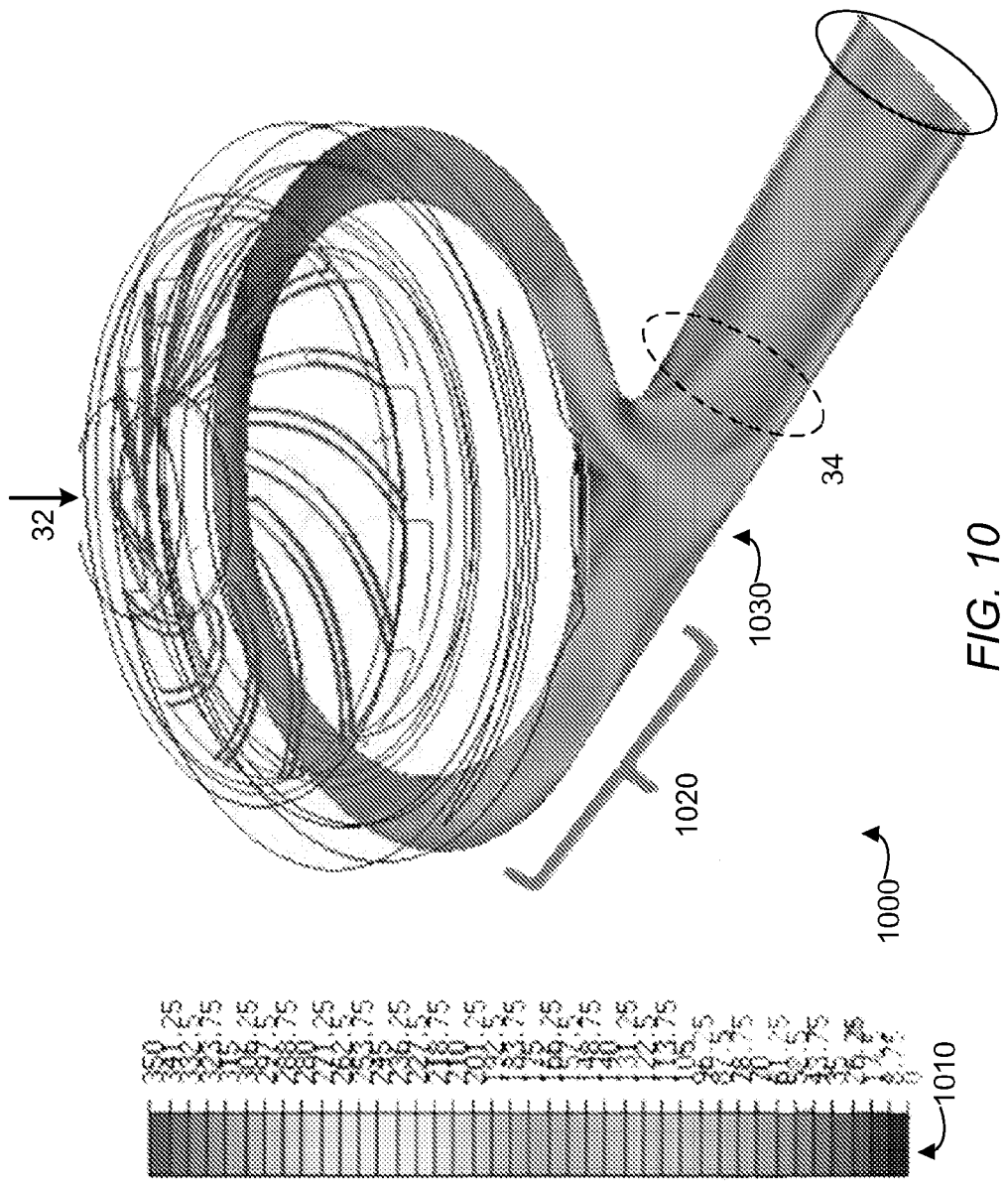
FIG. 10 illustrates a computational fluid dynamics (CFD) analysis of the velocity of a flow of gas in a blower housing during operation, according to certain embodiments.

FIG. 10 illustrates a computational fluid dynamics (CFD) analysis of the velocity of flowing gas in housing 22 during operation, resulting in spatial distribution 1000. This analysis includes an obstruction similar to or substantially the same as obstruction 15 of FIG. 8 (not shown in FIG. 10). Referring to FIG. 10, vertical scale 1010 indicates gas velocity, in inches per second, ranging from 0 to 350 inch/s. In the analysis for FIG. 10, area 1030 indicates a relatively less abrupt transition (compared to area 930 of FIG. 9) from comparatively lower velocity gas flow to comparatively higher velocity gas flow, near outlet 34. Area 1020 in FIG. 10 indicates a different proportion (compared to area 920 of FIG. 9) of comparatively lower velocity gas flow near/upstream from outlet 34. In some embodiments, obstruction 15 effectively mixes gas flows having different velocities less abruptly, and/or further away from outlet 34, thereby changing the proportion of comparatively lower velocity gas flow near/upstream from outlet 34. As a result, spatial distribution 1000 of FIG. 10 reflects less collisions between gas flows having different velocities, less vortices as a result thereof, and/or reduced noise generation compared to spatial distribution 900 of FIG. 9.

Figure 11:
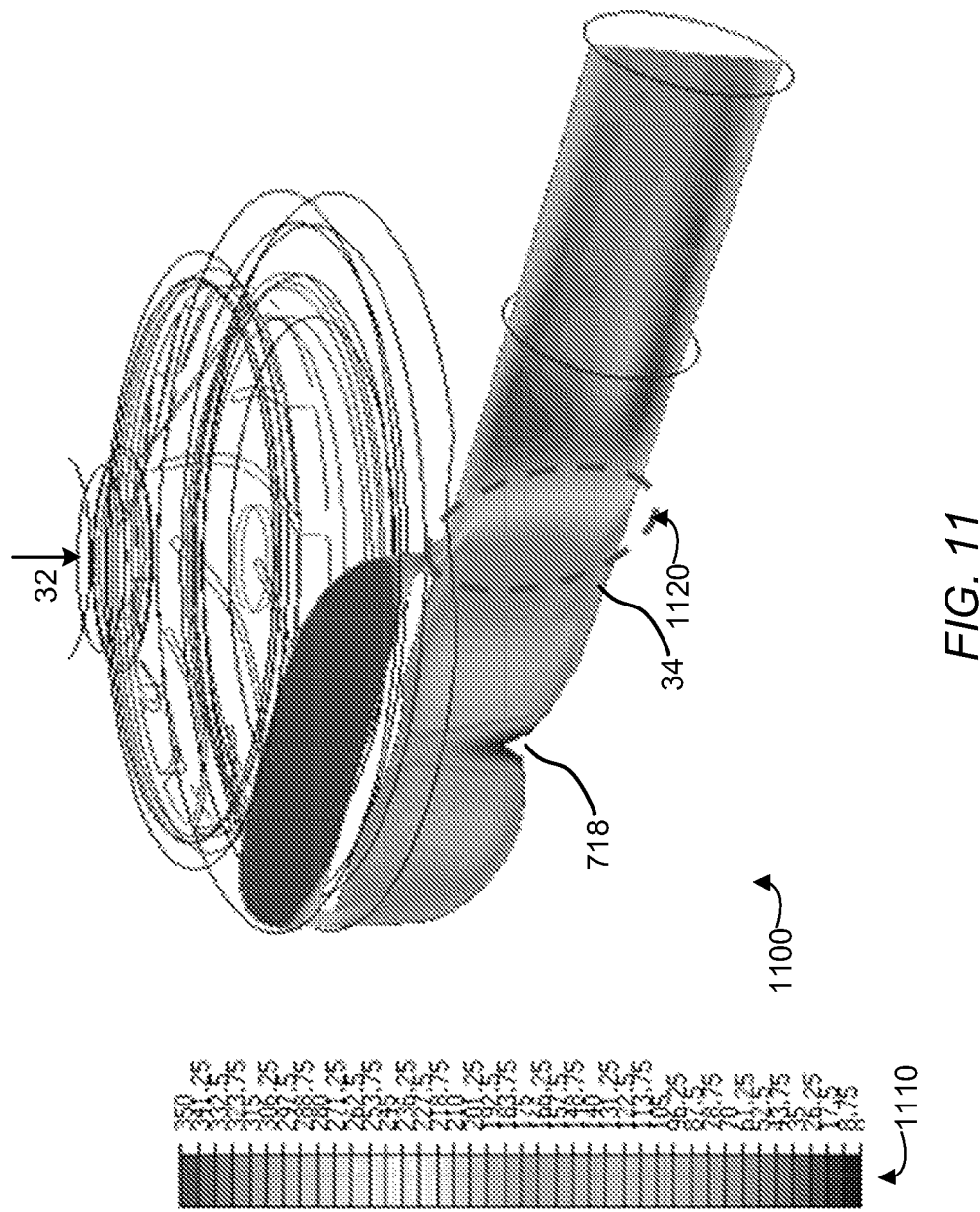
FIG. 11 illustrates a computational fluid dynamics (CFD) analysis of the velocity of a flow of gas in a blower housing during operation.

FIG. 11 illustrates a computational fluid dynamics (CFD) analysis of the velocity of flowing gas in a blower housing during operation, resulting in spatial distribution 1100. This analysis does not include an obstruction similar to or substantially the same as obstruction 15 of FIG. 8. Referring to FIG. 11, vertical scale 1110 indicates gas velocity, in inches per second, ranging from 0 to 350 inch/s. In the analysis for FIG. 11, area 1120 indicates a relatively abrupt transition from comparatively lower velocity gas flow to comparatively higher velocity gas flow, near outlet 34. In some cases, vortices 718 may be indicated by a very low velocity gas flow.

Figure 12:
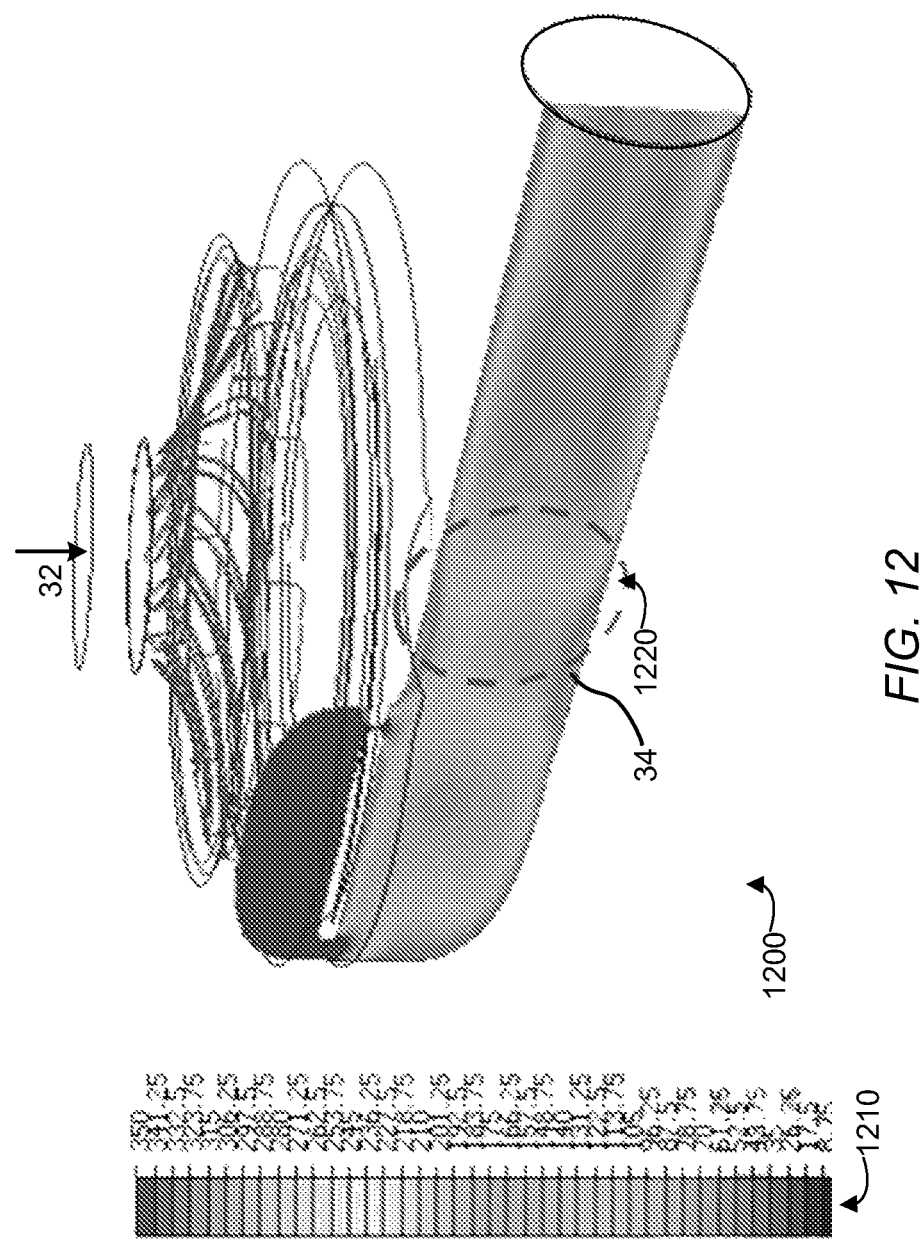
FIG. 12 illustrates a computational fluid dynamics (CFD) analysis of the velocity of a flow of gas in a blower housing during operation, according to certain embodiments.

FIG. 12 illustrates a computational fluid dynamics (CFD) analysis of the velocity of flowing gas in housing 22 during operation, resulting in spatial distribution 1200. This analysis includes an obstruction similar to or substantially the same as obstruction 15 of FIG. 8 (not shown in FIG. 12). Referring to FIG. 12, vertical scale 1210 indicates gas velocity, in inches per second, ranging from 0 to 350 inch/s. In the analysis for FIG. 12, area 1220 indicates a relatively less abrupt transition (compared to area 1120 of FIG. 11) from comparatively lower velocity gas flow to comparatively higher velocity gas flow, near outlet 34. In some embodiments, obstruction 15 effectively mixes gas flows having different velocities less abruptly, and/or further away from outlet 34. As a result, spatial distribution 1200 of FIG. 12 reflects less collisions between gas flows having different velocities, less vortices as a result thereof, and/or reduced noise generation compared to spatial distribution 1100 of FIG. 11.

Figure 13:
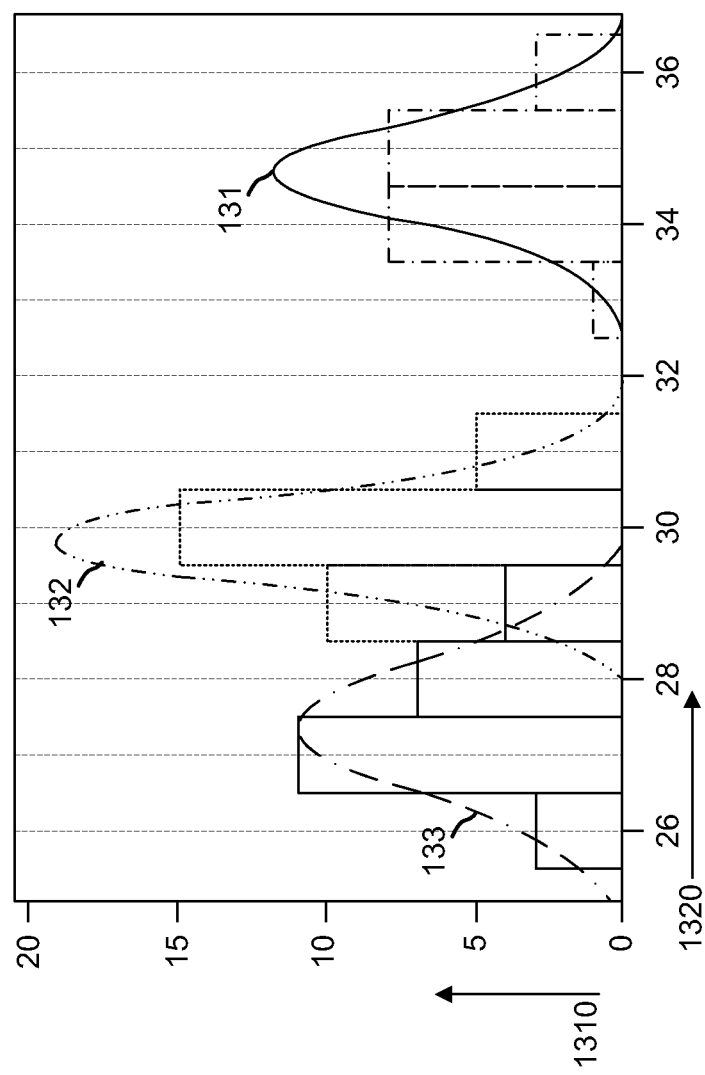
FIG. 13 illustrates noise pressure levels of various blower housing embodiments.

FIG. 13 illustrates overall noise pressure levels (or noise distributions) of various blower housing embodiments. Vertical axis 1310 indicates frequency of items tested. Horizontal axis 1320 indicates overall noise pressure level, in dBA. Noise distribution 131 reflects an older generation respiratory therapy device including a blower (not including an obstruction the same as or similar to obstruction 15 of FIG. 8). Referring to FIG. 13, noise distribution 131 is primarily distributed from 33 dBA to 37 dBA, with the mean being about 34.7 dBA and a standard deviation of about 0.67. Noise distribution 132 reflects a newer generation respiratory therapy device including a blower, but not including an obstruction similar to or substantially to same as obstruction 15 of FIG. 8. Referring to FIG. 13, noise distribution 132 is primarily distributed from 28 dBA to 32 dBA, with the mean being about 29.8 dBA and a standard deviation of about 0.62. Noise distribution 133 reflects device 70 included in a respiratory therapy device, and including obstruction 15 (not shown in FIG. 13). Noise distribution 132 is primarily distributed from 25 dBA to 30 dBA, with the mean being about 27.4 dBA and a standard deviation of about 0.89. Note that the overall noise pressure level is reduced, in device 70, by approximately 2.4 dBA.

Figure 14:
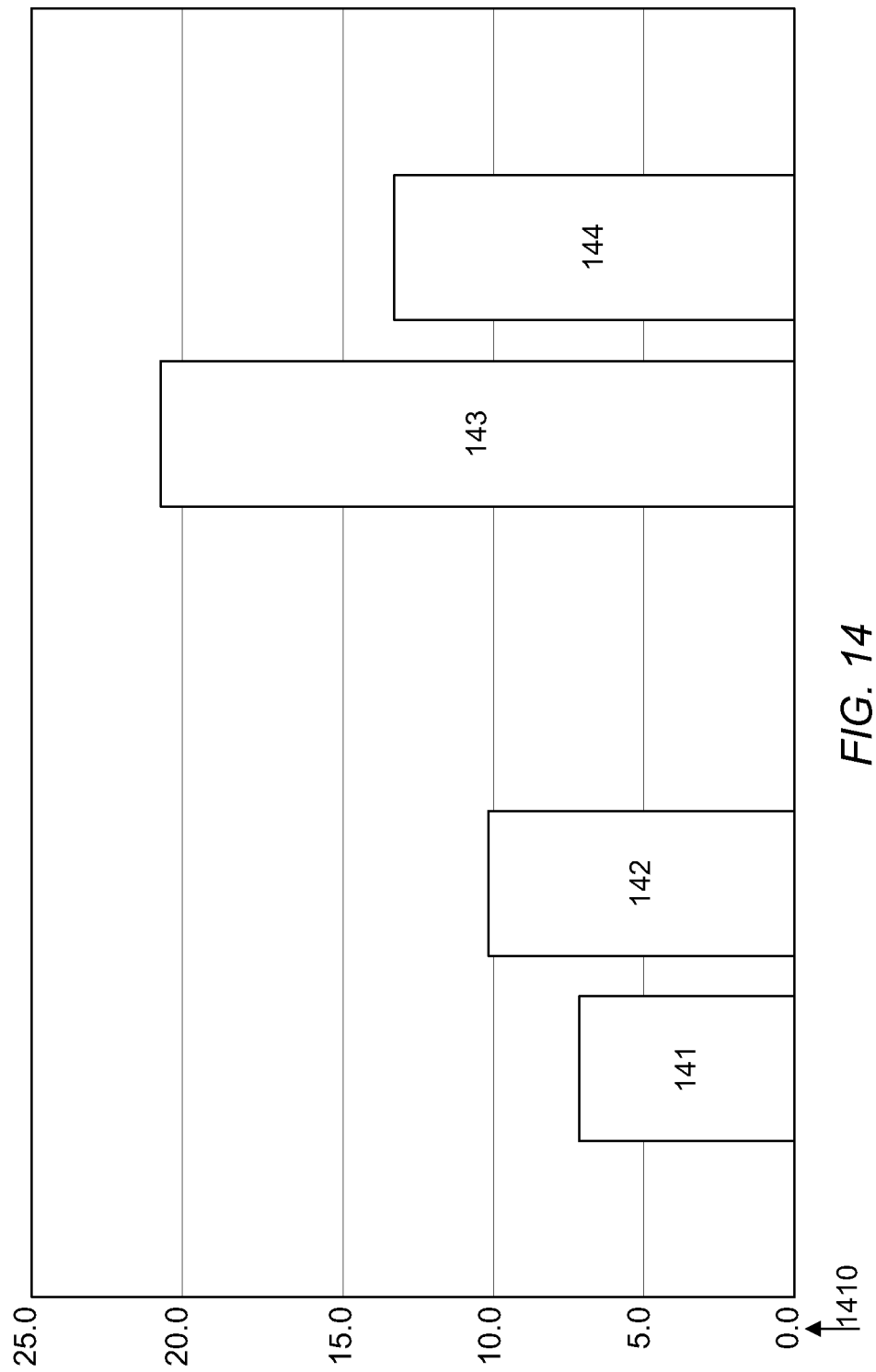
FIG. 14 illustrates tonal noise pressure levels of various blower housing embodiments.

FIG. 14 illustrates tonal noise pressure levels of various blower housing embodiments. Vertical axis 1410 indicates tonal noise pressure level (or noise level), in dBA. Noise level 143 reflects tonal noise at 204 Hz, of 21.5 dBA for a newer generation respiratory therapy device including a blower, but not including an obstruction similar to or substantially to same as obstruction 15 of FIG. 8. Referring to FIG. 14, noise level 144 reflects tonal noise at 408 Hz, of 13.6 dBA for the same device/configuration as noise level 143. Noise level 141 reflects tonal noise at 204 Hz, of 7.2 dBA for device 70 included in a respiratory therapy device, and including obstruction 15. Noise level 142 reflects tonal noise at 408 Hz, of 10.2 dBA for the same device/configuration (device 70 with obstruction 15, not shown in FIG. 14) as noise level 141. Note that the tonal noise pressure level is reduced, in device 70, by approximately 3.4 dBA at 408 Hz, and by approximately 14.3 dBA at 204 Hz.

Figure 16:
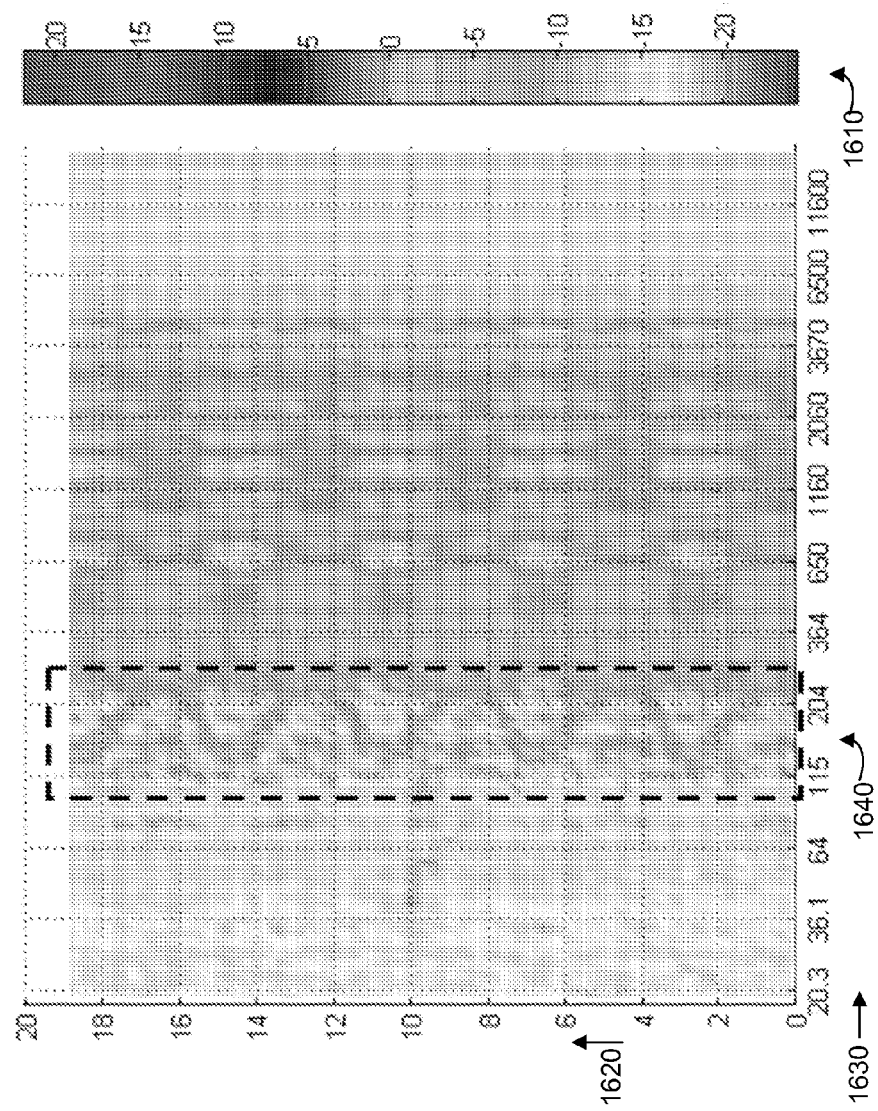
FIG. 16 illustrates dynamic noise pressure levels over multiple respiratory cycles.

FIG. 16 illustrates dynamic noise pressure levels determined over multiple respiratory cycles for a respiratory therapy device, resulting in a noise distribution 1600. Vertical scale 1610 indicates noise pressure level, in dBA, ranging from −20 to 20 dBA. Vertical axis 1620 indicates time, in seconds. Noise distribution 1600 covers approximately 19 seconds of usage of a respiratory therapy device, spanning approximately five breathing cycles. The configuration used to determine noise distribution 1600 does not include an obstruction similar to or substantially the same as obstruction 15 of FIG. 8. Referring to FIG. 16, horizontal axis 1630 indicates frequency, in Hz, ranging from 20.3 to approximately 20 kHz. Area 1640 indicates noise, including tonal noise, that is both time-varying—with a periodicity similar to or substantially the same as the respiratory rate—and frequency-varying between, approximately, 115 Hz and 204 Hz. This kind of noise may be undesirable.

Figure 17:
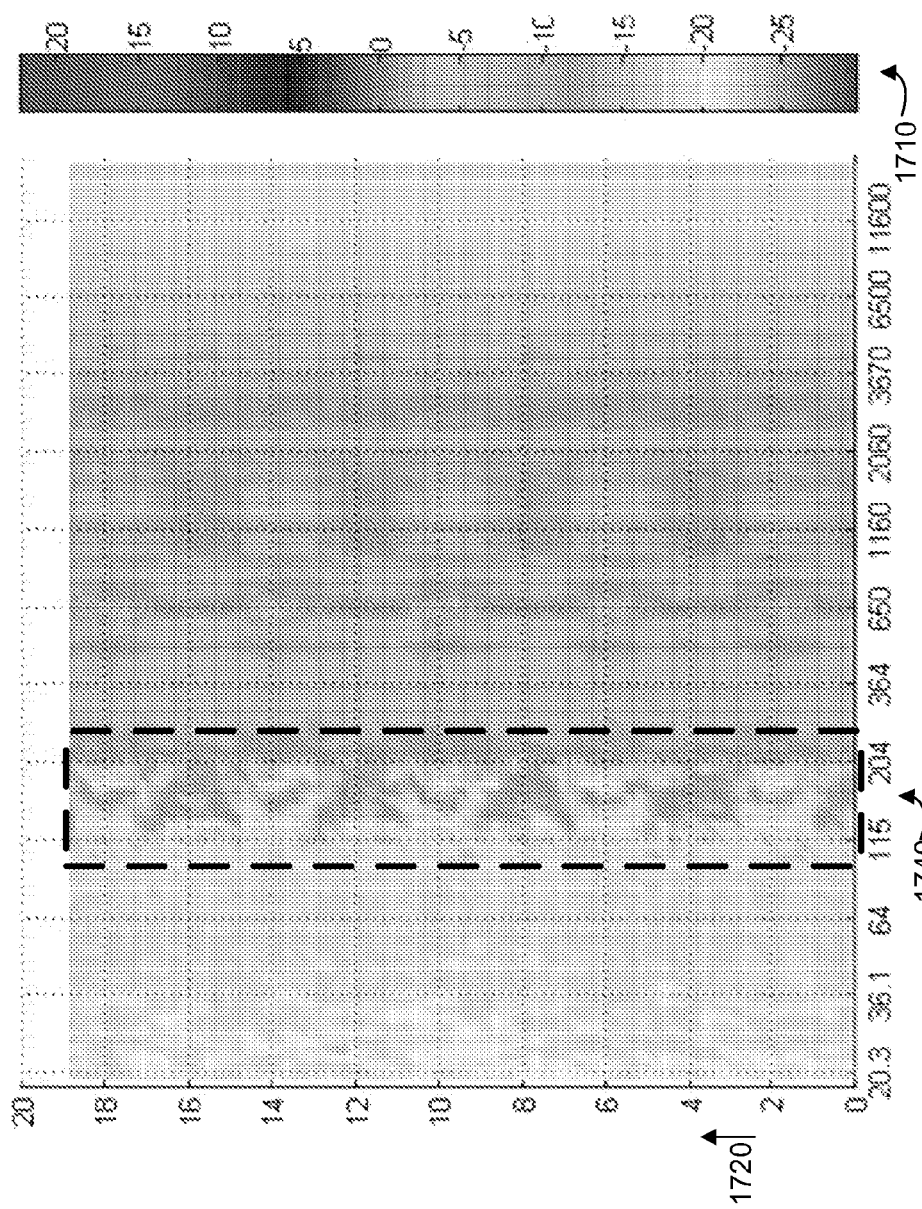
FIG. 17 illustrates dynamic noise pressure levels over multiple respiratory cycles, according to certain embodiments.

FIG. 17 illustrates dynamic noise pressure levels determined over multiple respiratory cycles for a respiratory therapy device according to certain embodiments, resulting in a noise distribution 1700. Vertical scale 1710 indicates noise pressure level, in dBA, ranging from −20 to 20 dBA. Vertical axis 1720 indicates time, in seconds. Noise distribution 1700 covers approximately 19 seconds of usage of a respiratory therapy device, spanning approximately five breathing cycles. The configuration used to determine noise distribution 1700 includes an obstruction (not shown) similar to or substantially the same as obstruction 15 of FIG. 8. Referring to FIG. 17, horizontal axis 1730 indicates frequency, in Hz, ranging from 20.3 to approximately 20 kHz. Area 1740 indicates that the noise level, compared to area 1640 in FIG. 16, now includes less noise, in particular less time-varying noise and less frequency-varying noise in the range between, approximately, 115 Hz and 204 Hz. Note that noise distribution 1700 may be preferred compared to noise distribution 1600 of FIG. 16.

Figure 18:
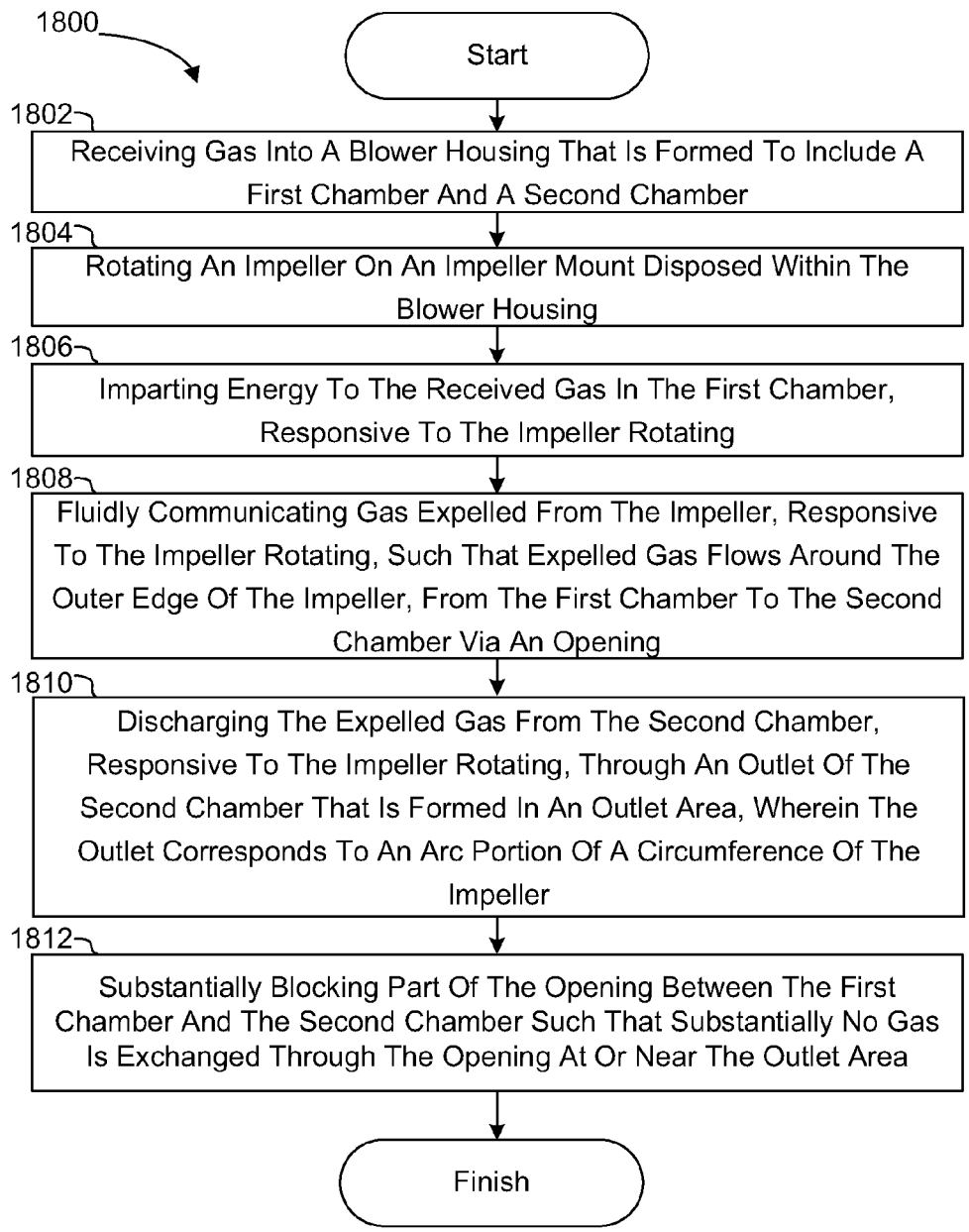
FIG. 18 illustrates a method for reducing noise of a device for blowing gas from an inlet to an outlet, according to certain embodiments.

FIG. 18 illustrates a method for reducing noise of a device for blowing gas from an inlet to an outlet. The operations of method 1800 presented below are intended to be illustrative. In certain embodiments, method 1800 may be accomplished with one or more additional operations not described, and/or without one or more of the operations discussed. Additionally, the order in which the operations of method 1800 are illustrated in FIG. 18 and described below is not intended to be limiting.

In certain embodiments, method 1800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1800 in response to instructions stored electronically on an electronic storage medium. The one or more processing devices may include one or more devices configured through hardware, firmware, and/or software to be specifically designed for execution of one or more of the operations of method 1800.

At an operation 1802, gas is received into a blower housing that is formed to include a first chamber and a second chamber. In one embodiment, operation 1802 is performed by an inlet similar to or substantially the same as inlet 32 (shown in FIG. 7 and described above).

At an operation 1804, an impeller is rotated on an impeller mount disposed within the blower housing. In one embodiment, operation 1804 is performed by an impeller mount similar to or substantially the same as impeller mount 8 (shown in FIG. 7 and described above).

At an operation 1806, energy is imparted to the received gas. In one embodiment, operation 1806 is performed by an impeller similar to or substantially the same as impeller 20 (shown in FIG. 7 and described above).

At an operation 1808, gas expelled from the impeller is fluidly communicated from the first chamber to the second chamber, such that expelled gas flows around the outer edge of the impeller and into the second chamber. In one embodiment, operation 1808 is performed by an opening similar to or substantially the same as opening 716 (shown in FIG. 7 and described above).

At an operation 1810, the expelled gas is discharged from the second chamber through an outlet formed in an outlet area of the second chamber. The outlet corresponds to an arc portion of a circumference of the impeller. In one embodiment, operation 1810 is performed by an outlet similar to or substantially the same as outlet 34 (shown in FIG. 7 and described above).

At an operation 1812, part of the opening between the first chamber and the second chamber is substantially blocked such that substantially no gas is exchanged through the opening at or near the outlet area. In one embodiment, operation 1812 is performed by an obstruction similar to or substantially the same as obstruction 15 (shown in FIG. 7 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A device for blowing gas from an inlet to an outlet, the device including:
    an impeller, having a first side and a second side, the first side being configured to impart energy to the gas responsive to the impeller being rotated, the second side being opposite the first side and having a generally circular shape, wherein the impeller has a circumference;
    a blower housing configured to house the impeller;
    an impeller mount disposed within the blower housing, the impeller mount being configured to rotatably mount the impeller within the blower housing,
    wherein the blower housing is configured to form a first chamber and a second chamber,
    wherein the impeller is disposed within the first chamber such that the first chamber is divided from the second chamber at or near the second side of the impeller, and such that as the impeller rotates within the first chamber, the gas imparted with energy from the impeller is expelled from the impeller,
    wherein the second chamber is in fluid communication with the first chamber through an opening between the first chamber and the second chamber, wherein the opening is formed radially outward from an axis of rotation of the impeller to an outer edge of the impeller such that the gas that has been expelled from the impeller in the first chamber flows around the outer edge of the impeller and into the second chamber through the opening,
    wherein the second chamber includes an outlet such that the gas that flows into the second chamber is discharged from the blower housing through the outlet, the outlet being formed in the second chamber in an outlet area of the second chamber corresponding to an arc portion of the circumference of the impeller, and
    wherein the blower housing further includes an obstruction provided adjacent to the outlet, the obstruction being positioned radially outward from the axis of rotation of the impeller and comprising an arc-shaped surface spanning at least a fraction of the arc portion of the circumference of the impeller such that the opening between the first chamber and the second chamber is substantially blocked at or near the outlet area such that substantially no gas is exchanged between the first chamber and the second chamber through the opening at or near the outlet area.

2. The device of claim 1, wherein the obstruction spans an arc length ranging between 30 and 120 degrees of the circumference of the impeller at or near the outlet area.

3. The device of claim 1, wherein the obstruction spans at least half of the arc portion corresponding to the outlet area of the second chamber.

4. The device of claim 1, wherein the obstruction is configured to substantially block the opening such that vortices caused by a collision of a high-velocity flow of the gas with a low-velocity flow of the gas are reduced.

5. The device of claim 1, wherein the obstruction is configured to substantially block the opening such that one or both of tonal noise and/or broadband noise in a range of high human auditory sensitivity is reduced.

6. The device of claim 1, wherein the outlet comprises a gas outlet channel that extends circumferentially around the impeller and that is separated from the opening by a ledge.

7. A method for reducing noise of a device for blowing gas from an inlet to an outlet, the method including:
    receiving the gas through an inlet of a blower housing that is formed to include a first chamber and a second chamber;
    rotating an impeller on an impeller mount disposed within the blower housing;
    imparting energy to the received gas in the first chamber, responsive to the impeller rotating;
    fluidly communicating the gas expelled from the impeller, responsive to the impeller rotating, such that expelled gas flows around the outer edge of the impeller, from the first chamber to the second chamber via an opening;
    discharging the expelled gas from the second chamber, responsive to the impeller rotating, through an outlet of the second chamber that is formed in an outlet area, wherein the outlet corresponds to an arc portion of a circumference of the impeller; and
    substantially blocking the opening between the first chamber and the second chamber via an obstruction such that substantially no gas is exchanged through the opening at or near the outlet area,
    wherein the obstruction is provided adjacent to the outlet and positioned radially outward from an axis of rotation of the impeller, and wherein the obstruction comprises an arc-shaped surface spanning at least a fraction of the arc portion of the circumference of the impeller.

8. The method of claim 7, wherein the step of substantially blocking part of the opening between the first chamber and the second chamber is accomplished by the obstruction spanning an arc length ranging between 30 and 120 degrees of the circumference of the impeller at or near the outlet area.

9. The method of claim 7, wherein the step of substantially blocking part of the opening between the first chamber and the second chamber is accomplished by the obstruction spanning at least half of the arc portion corresponding to the outlet area of the second chamber.

10. The method of claim 7, wherein the step of substantially blocking part of the opening between the first chamber and the second chamber is performed by the obstruction such that vortices caused by a collision of a high-velocity flow of the gas with a low-velocity flow of the gas are reduced.

11. The method of claim 7, wherein the step of substantially blocking part of the opening between the first chamber and the second chamber is performed by the obstruction such that one or both of tonal noise and/or broadband noise in a range of high human auditory sensitivity is reduced.

12. The method of claim 7, wherein the outlet comprises a gas outlet channel that extends circumferentially around the impeller and is separated from the opening by a ledge, and wherein the discharging the expelled gas from the second chamber through the outlet includes discharging through the gas outlet channel.

13. A system configured to reduce noise of a device for blowing gas from an inlet to an outlet, the system including:

means for receiving the gas into a blower housing that is formed to include a first chamber and a second chamber;

rotating means for imparting energy to the received gas in the first chamber;

mounting means for rotating the rotating means, wherein the mounting means is disposed within the blower housing;

communicating means for fluidly communicating the gas expelled from the rotating means, such that expelled gas flows around the outer edge of the rotating means, from the first chamber to the second chamber;

discharging means for discharging the expelled gas from the second chamber, that is formed in a discharge area of the second chamber, wherein the discharging means corresponds to an arc portion of a circumference of the rotating means; and blocking means for substantially blocking the communicating means between the first chamber and the second chamber such that substantially no gas is exchanged through the communicating means at or near the discharge area, wherein the blocking means is provided adjacent to the discharging means and positioned radially outward from an axis of rotation of the rotating means, and wherein the blocking means comprises an arc-shaped surface spanning at least a fraction of the arc portion of the circumference of the rotating means.

14. The system of claim 13, wherein the blocking means spans an arc length ranging between 30 and 120 degrees of the circumference of the rotating means at or near the discharge area.

15. The system of claim 13, wherein the blocking means spans at least half of the arc portion corresponding to the discharge area.

16. The system of claim 13, wherein the blocking means reduces vortices caused by a collision of a high-velocity flow of the gas with a low-velocity flow of the gas.

17. The system of claim 13, wherein the blocking means reduces one or both of tonal noise and/or broadband noise in a range of high human auditory sensitivity.

18. The system of claim 13, wherein the discharging means comprises a channel that extends circumferentially around the rotating means and is separated from the communicating means by a ledge.

* * * * *